United States Patent [19]

Grimmer et al.

[11] Patent Number: 4,687,847

[45] Date of Patent: Aug. 18, 1987

[54] PURIFICATION OF RIBOFLAVIN

[75] Inventors: Johannes Grimmer, Grenaa, Denmark; Hans C. Horn, Lambsheim, Fed. Rep. of Germany

[73] Assignee: BASF Aktiengesellschaft, Ludwigshafen, Fed. Rep. of Germany

[21] Appl. No.: 743,157

[22] Filed: Jun. 10, 1985

[30] Foreign Application Priority Data

Jun. 12, 1984 [DE] Fed. Rep. of Germany ....... 3421714

[51] Int. Cl.$^4$ .......................................... C07D 475/14
[52] U.S. Cl. .................................... 544/251
[58] Field of Search .................. 544/251; 514/251

[56] References Cited

U.S. PATENT DOCUMENTS

| 2,324,800 | 7/1943 | Pasternack et al. | 544/251 |
| 2,374,661 | 5/1945 | Bergel et al. | 544/251 |
| 2,531,439 | 11/1950 | Jordan | 544/251 X |
| 2,603,633 | 7/1952 | Dale | 544/251 |
| 2,797,215 | 6/1957 | Dale | 544/251 |
| 2,807,611 | 9/1957 | Howe | 544/251 |
| 4,567,261 | 1/1986 | Ernst et al. | 544/251 |
| 4,567,262 | 1/1986 | Grimmer et al. | 544/251 |

OTHER PUBLICATIONS

Fermente Hormone-Vitamine, vol. III/1, Georg Thieme Verlag Stuttgart, 1974, p. 631.
Ullmanns Encyclopedia of Technischen Chemie, vol. 23, Verlap Chemie, Weinheim, 1983, p. 664.

Primary Examiner—Donald G. Daus
Assistant Examiner—Diana G. Rivers
Attorney, Agent, or Firm—Oblon, Fisher, Spivak, McClelland & Maier

[57] ABSTRACT

Very pure riboflavin (I) is obtained by a process in which the riboflavin is dissolved in dilute aqueous alkali metal hydroxide solution, if necessary the alkaline solution is purified by treatment with active carbon or with a solvent which is insoluble or only slightly soluble in water, the resulting alkaline solution of I is introduced into water which is at 90°–100° C. and to which an acid has been added in an amount such that the reaction mixture is brought to a pH of from 6.5 to 0.8, the temperature being maintained at from 40° to 100° C., the reaction mixture is kept at from 90° to 100° C. for from 10 to 80 minutes and cooled, and I is then isolated.

9 Claims, No Drawings

PURIFICATION OF RIBOFLAVIN

The present invention relates to a process for producing very pure riboflavin from crude riboflavin (I; vitamin $B_2$) by dissolving the latter in dilute aqueous alkali metal hydroxide solution, if necessary purifying this solution, and isolating the riboflavin by introducing the solution into aqueous acid solution at from 90° to 100° C.

It is well known (cf. for example W. H. Sebrell and R. S. Harris, The Vitamins; Chemistry, Physiology, Pathology, Methods, 2nd edition, volume V, 1982, Academic Press, page 22) that riboflavin is usually synthesized by condensation of an N-(D)-ribityl-2-arylazo-4,5-dimethylaniline (II) with barbituric acid (III).

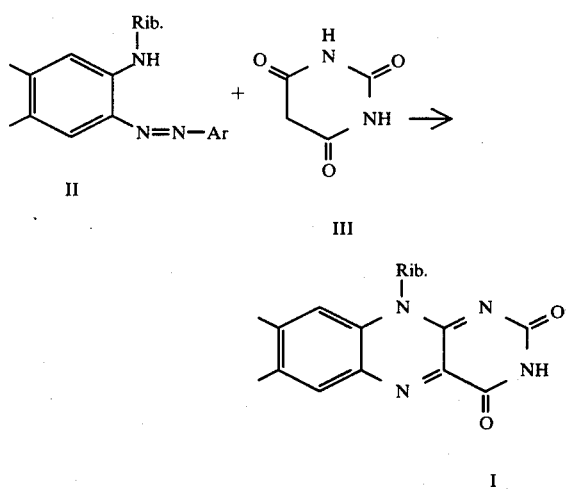

Rib=D-ribityl
Ar=aryl, e.g. phenyl

This procedure gives a crude product which, in addition to about 92–96% by weight of I, also contains various impurities including, for example, barbituric acid, dibarbituric acid, lumiflavin, lumichrome and N-(D)-ribityl-6-arylazo-4,5-dimethylaniline.

The condensation of other N-(D)-ribityl-4,5-dimethylaniline derivatives with barbituric acid derivatives to give riboflavin has also been described.

Moreover, the formation of riboflavin by a biosynthetic route with the aid of microorganisms is known from the literature.

Since the recovery of pure riboflavin from the crude product by crystallization processes alone entails disproportionate expense, U.S. Pat. No. 2,324,800 describes a method in which the crude riboflavin is subjected to an oxidative treatment in an aqueous acidic medium, after which any precipitates are separated off and the remaining solution is diluted with a large amount of water. This procedure gives the riboflavin in the form of yellow needles which need only be filtered off and washed.

The disadvantages of this process are that about 15% of the riboflavin used is lost during this purification process, the procedure is time-consuming and technically troublesome, and the product I obtained still contains traces of organic compounds, such as aniline, which present problems when it is used for human nutrition.

It is an object of the present invention to provide a process for producing a very pure product I, which overcomes the disadvantages of the prior art, ie. which is technically more advantageous and in which a smaller amount of I is lost during the purification process and an even purer product I is obtained.

We have found that this object is achieved by a process for the purification of crude riboflavin, wherein (a) the riboflavin to be purified is suspended in water and brought into solution by the addition of an aqueous solution of an alkali metal hydroxide, or the riboflavin is dissolved in about 0.16–0.63 molar aqueous alkali metal hydroxide solution, (b) if necessary, the resulting alkaline riboflavin solution is purified by treatment with active carbon or a filtration aid followed by filtration, or by extraction with an inert solvent which is insoluble or only slightly soluble in water, (c) while a temperature of from 40° to 100° C., preferably about 97°–99° C., is maintained, the alkaline riboflavin solution obtained is introduced into water which is at about 90°–100° C. and to which an acid has been added in an amount such that the pH of the reaction mixture is brought to 6.5–0.8, (d) the reaction mixture is heated at about 90°–100° C. for about a further 10–80, preferably 20–60, minutes, if necessary while stirring, and (e) the reaction mixture is cooled and the riboflavin which has crystallized out is isolated.

In a particularly advantageous embodiment of the process, the temperature of the alkaline riboflavin solution in reaction steps (a) and (b) is about 10°–50° C., preferably about 30°–45° C., or the temperature exceeds 50° C. for only a short time, if at all.

Losses of I in the novel purification process are substantially lower than in the case of a purification in acidic solution. This is very surprising since the literature relating to I, even the most recent literature (cf. Fermente - Hormone - Vitamine, volume III/1, Georg Thieme Verlag Stuttgart, 1974, page 631 and Ullmanns Encyklopadie der technischen Chemie, volume 23, Verlag Chemie, Weinheim, 1983, page 664), states that I readily decomposes in alkaline solution.

Although U.S. Pat. No. 2,603,633 discloses a process for the preparation of 3 different types of crystals I, in which these crystals are obtained by the addition of an acid to an alkaline solution of I at from 10° to 25° C., attempts to use the crystallization processes described for the purification of I on an industrial scale did not give acceptable results.

In contrast, the novel process gives riboflavin in a yield of from 90 to 92% of theory and with a purity of more than 99.5% (determined according to the European Pharmacopeia).

The novel process is suitable for producing a very pure product from crude I containing about 10–99.5% of I, as obtained in the microbiological preparation procedure or in the synthesis.

To carry out the novel process, the crude I is first suspended in water, the amount of water generally used being about 1130–6580 g, preferably about 1880–3760 g, per mole of I. Advantageously, the water used is at from 25° to 50° C. or preferably from 35° to 45° C.

An aqueous solution of an alkali metal hydroxide is added to this aqueous suspension of I in an amount such that the suspended I goes completely into solution. Preferably, aqueous KOH or NaOH, in particular the industrially very readily available and cheap NaOH in the form of about 25% strength solution, is used as the aqueous solution of an alkali metal hydroxide. About 1-1.25 moles of alkali metal hydroxide per mole of I are required to dissolve the latter; for 25% strength NaOH, this means about 0.5 kg per kg of I. However, the riboflavin can also be dissolved directly in dilute aqueous alkali metal hydroxide solution. For this purpose, about 0.16-0.63, preferably about 0.28-0.32, molar aqueous KOH or NaOH is used in amounts of about 17.5-5, preferably from 10 to 9, kg per kg of I, depending on the concentration of the alkali metal hydroxide solution used.

I is generally dissolved at from about 10° to 50° C., preferably from 25° to 50° C., in particular from 30° to 45° C. If I is in contact with the aqueous alkaline solution for only a short time, as is the case in a continuous procedure, temperatures higher than 50° C., e.g. from 50° to 60° C., may also be used.

The resulting aqueous alkaline solution of I can then be purified. This can be done by treatment with active carbon followed by filtration, or by extraction with an inert solvent which is immiscible or only poorly miscible with water. The active carbon used may be virtually any commercially available grade.

Examples of suitable solvents for the extraction are ethyl acetate, chloroform and petroleum ether, in particular isobutyl acetate and n-butyl acetate.

In the purification of crude I prepared by a microbiological route, the aqueous alkaline solution of I is preferably purified by treatment with a filtration aid followed by filtration. The type of filtration aid used is not critical, it only being important to ensure that the rate of filtration is sufficiently high. For example Celite ® from Johns-Manville, USA, has proven useful.

The resulting I solution, which may or may not have been purified, is then introduced into water which is at from 96° to 100° C., preferably from 96° to 99° C., and to which an acid has been added in an amount such that the pH of the reaction mixture is brought to 6.5-0.8, preferably 6-1, the temperature being maintained at from 90° to 100° C., preferably from 96° to 99° C. In special cases, particularly where riboflavin prepared by a microbial route is being purified, it is also possible for the purified or unpurified solution of I to be introduced into the acidified hot water while maintaining somewhat lower temperatures, ie. about 40°-100° C.

The amount of water is such that the reaction mixture contains about 18-30, preferably about 20-25, kg of water per kg of I after the addition of the alkaline solution.

Acids which are added to the water are any acids which are as strong as or stronger than acetic acid, ie. those which have a $pK_a$ of 4.76 or lower and do not attack the riboflavin under the reaction conditions. Advantageously, the conventional mineral acids, such as HCl ($pK_a$ −6), $H_2SO_4$ ($pK_a$ −3), $HNO_3$ ($pK_a$ −1.32) or $H_3PO_4$ ($pK_a$ 2.09), are used, but organic acids, such as formic acid ($pK_a$ 3.77) and acetic acid ($pK_a$ 4.76), may also be employed. The use of nitric acid has proven particularly advantageous since it apparently has a mild oxidizing effect on the by-products in I, even in very dilute aqueous solution. When $HNO_3$ is used, pure I is obtained in a color which, in its brilliance, differs substantially from the color obtained using the other acids.

The mineral acid is used in an amount such that, on the one hand, the alkali metal hydroxide solution used is completely neutralized and, on the other hand, the solution becomes acidic so that the I is advantageously and completely precipitated. Where mixtures are purified without intermediate treatment with active carbon or an extracting agent, it is advisable to acidify the mixture to a pH below 3 in order that any by-products present are more readily destroyed during heating.

In general, about 1.06-3.5 moles of acid per mole of I are required for this purpose, depending on the amount of alkali metal hydroxide solution used.

The effective yield of I in the purification process can be further improved if bulk materials permitted for the particular intended use in animal nutrition or the pharmaceutical industry are added to the aqueous acidic solution obtained according to the invention in reaction step (e).

The advantageous effect can probably be explained by the fact that, in this procedure, the adsorption behavior of I is utilized in such a way that the 4-7% of by-products adsorbed onto the crude I is replaced by insoluble additives permitted in animal nutrition and the pharmaceutical industry.

Examples of bulk materials permitted in the pharmaceutical industry are corn starch, corn cob flour, fine soybean flour and wheat bran. Examples of additives permitted in animal nutrition are $SiO_2$, calcium silicates, kieselguhr, steatite, talc and bolus alba (white clay). The additives are used in general in amounts of from 1 to 500 g per kg of I.

EXAMPLE 1

Dependence of the yield of I on the concentration of the alkali metal hydroxide solution 40 g of riboflavin were suspended in 400 ml of water, the suspension was heated to 40° C., the amount of a 25% strength NaOH shown in Table 1 was introduced into the suspension, and the reaction mixture was stirred for 15 minutes at 40° C. The alkaline solution was then added in the course of 20 minutes to a mixture of 400 ml of water and the amount of a concentrated (37% strength) hydrochloric acid shown in Table 1, this mixture being at 98° C. The alkaline residues were flushed in with water, the reaction mixture was stirred for 1 hour at 98°-100° C. and then cooled to 40° C., and the precipitate was filtered off under suction, washed with 400 ml of water at 60° C. and 200 ml of methanol and dried at 80°-100° C. The yield was calculated from the amount of I weighed out.

TABLE 1

| Example | 25% strength NaOH [g] | 37% strength HCl [g] | Yield [g] | [% of theory] |
|---|---|---|---|---|
| 1a | 20 | 30 | 38.7 | 96.75 |
| 1b | 40 | 60 | 38.4 | 96.00 |
| 1c | 60 | 90 | 37.8 | 94.50 |

EXAMPLE 2

Yield of I as a function of the temperature of the alkaline solution of I 40 g of I in each case were suspended in 400 ml of water, 20 g of a 25% strength NaOH solution were added to the suspension, and the stirred mixture was then heated for 15 minutes at the temperature shown in Table 2. Working up of the reaction mixture and determination of the yield were carried out as described in Example 1a.

TABLE 2

| Example | Temperature [°C.] | Yield [g] | Yield [% of theory] |
| --- | --- | --- | --- |
| 2a | 30 | 38.7 | 96.75 |
| 2b | 40 | 38.8 | 97.00 |
| 2c | 50 | 38.4 | 96.00 |
| 2d | 60 | 37.7 | 94.25 |
| 2e | 70 | 34.9 | 87.25 |

EXAMPLE 3

Yield of I as a function of the HCl concentration 40 g of I in each case were suspended in 400 ml of water, the suspension was heated to 40° C., 20 g of a 25% strength NaOH solution were introduced, and the stirred reaction mixture was heated at 40° C. for 15 minutes. Thereafter, the alkaline solution was added in the course of 20 minutes to a mixture of 400 ml of water and the amount of a 37% strength HCl shown in Table 3, this mixture being at 98° C. Working up of the reaction mixture and determination of the yield were carried out as described in Example 1 a.

TABLE 3

| Example | 37% strength HCl [g] | Yield [g] | Yield [% of theory] |
| --- | --- | --- | --- |
| 3a | 30 | 38.9 | 97.25 |
| 3b | 40 | 38.6 | 96.50 |
| 3c | 50 | 38.3 | 95.75 |
| 3d | 60 | 38.5 | 96.25 |

EXAMPLE 4

Additional purification with active carbon 40 g of a 93% strength crude riboflavin were suspended in 400 ml of water at 40° C., 20 g of a 25% strength NaOH were added to the suspension, followed by the addition of 1 g of type 2S active carbon from Chemviron, and the stirred mixture was heated for 15 minutes at 40° C. Thereafter, the solution was filtered under suction over a G4 glass filter, and the residue was washed with water. The combined filtrates were pumped in the course of 30 minutes into a mixture of 400 ml of water and 30 g of a 37% strength HCl, this mixture being at 98° C. The stirred reaction mixture was heated at 98°-100° C. for a further hour and then left to cool to 40° C., and the product I was isolated as described in Example 1a.

The yield was 35.7 g, corresponding to 89.25% of theory, the purity was 99.9% (European Pharmacopeia) and the aniline content was about 3 ppm.

EXAMPLE 5

Additional extraction with isobutyl acetate 40 g of 93% strength crude I in each case were suspended in 500 ml of water, 20 g of a 25% strength NaOH solution were added to the suspension, and the resulting solution was stirred for a further 15 minutes at room temperature. Thereafter, the mixture was extracted by shaking with 150 ml of isobutyl acetate and then with 100 ml of isobutyl acetate. The organic phases were separated off and the aqueous alkaline solution was then introduced into a mixture of 300 ml of water and 30 g of a 37% strength HCl, this mixture being at about 98° C. The stirred reaction mixture was heated for a further hour at 98°-100° C. and then left to cool, and working up was carried out as described in Example 1.

The yield was 35.3 g, corresponding to 88.25% of theory, and the purity was 100.1% (European Pharmacopeia).

The organic phase separated off contained 1.3 g of dry substance, about half of which consisted of N-(D)-ribityl-6-phenylazo-4,5-dimethylaniline, which is useless for the preparation of I, and a large number of unidentified products.

EXAMPLE 6

(a) Alkaline purification with the addition of corn starch to I 40 g of crude I (93% strength) were suspended in 400 ml of water, the suspension was heated to 40° C., 20 g of a 25% strength NaOH were added, followed by the addition of 1 g of active carbon, and the resulting mixture was kept at 40° C. for 15 minutes, while stirring. Thereafter, the carbon was separated off over a G4 glass filter, the residue was washed riboflavin-free with water, and the combined alkaline filtrates were introduced in the course of 8 minutes into a mixture of 400 ml of water and 30 g of concentrated HCl, this mixture being at 98° C. The stirred reaction mixture was kept at 98° C. for 1 hour and then cooled to 50° C., and 1.5 g of corn starch were added. Stirring was continued for 15 minutes at 40° C. after which the mixture was filtered under suction at and the product was washed with water and methanol as described in Example 1a and dried at 90°-100° C.

The yield was 36.8 g, corresponding to 98.9% of theory (taking info account corn starch).

Purification in hydrochloric acid, with the addition of corn starch to I 40 g of crude I (93% strength) were slowly introduced into 66 g of concentrated HCl, 27.5 g of water were added after about 3 minutes and the resulting solution was kept at 32°-34° C. for 30 minutes, while stirring. Thereafter, the solution of I in hydrochloric acid was added in the course of 9 minutes to 800 ml of water at about 98° C., and the reaction mixture was kept at this temperature for 1 hour. The mixture was cooled to 50° C., after which 1.5 g of corn starch were added, stirring was continued for 15 minutes at 40° C., and I was then filtered off under suction and washed and dried, these last two steps being carried out as described in Example 1a.

Yield: 36.0 g, corresponding to 96.8% of theory.

EXAMPLES 7-11

The amount of moist crude I as shown in Table 4 (corresponding in each case to 40 g of dry crude 93.8% strength I) was suspended in 400 ml of water, the suspension was heated to the temperature shown in the Table, and 20 g of a 25% strength NaOH were added. The mixture was stirred for 15 minutes at the stated temperature, after which the alkaline solution was introduced in the course of 30 minutes into a mixture, at 98° C., of 400 ml of water and the mineral acid shown in Table 4, the reaction mixture being brought to the pH shown in Table 4. Thereafter, the stirred reaction mixture was kept at 98°-100° C. for 1 hour and then cooled to 40° C., and the precipitate was filtered off under suction, washed with 400 ml of water at 60° C. and 200 ml of methanol and dried at 80°-100° C. The yields and purities of I are stated in Table 4. The purities were determined by the method described in the European Pharmacopeia, vol. 1.

TABLE 4

| Example | Moist crude I [g] | Acid | pH | Temperature [°C.] | Yield [g] | Yield (% of theory) | Purity [g] |
|---|---|---|---|---|---|---|---|
| 7 | 48.7 | 34.8 g of 65% strength $HNO_3$ | 0.85 | 30 | 35.8 | 95.4 | 100.5 |
| 8 | 49.1 | 31.0 g of 96% strength $H_2SO_4$ | 0.84 | 40 | 35.1 | 93.55 | 100.5 |
| 9 | 49.1 | 35.1 g of 85% strength $H_3PO_4$ | 0.98 | 40 | 35.8 | 95.4 | >99.9 |
| 10 | 49.0 | 14 g of 100% pure formic acid | 3.5 | 40 | 34.5 | 92.1 | >99.9 |
| 11 | 49.0 | 18.3 g of glacial acetic acid | 4.5 | 40 | 34.0 | 90.6 | >99.9 |

EXAMPLE 12

Purification of riboflavin prepared by fermentation 50 g of a 62% strength riboflavin prepared by a fermentation method and 20 g of the filtration aid Celite (Standard Super-Cel ® from Johns-Manville, U.S.A.) were suspended in 500 ml of water at 20° C., 18 g of a 25% strength aqueous NaOH were added to the suspension, and the mixture was stirred for 15 minutes and then filtered. The filter cake was washed riboflavin-free with 200 ml of water. The wash water was combined with the mother liquor, and the entire amount was pumped in the course of 30 minutes into a mixture of 100 ml of water and 27 g of concentrated hydrochloric acid, this mixture being at 98°–100° C. Stirring was continued for 1 hour at 98°–100° C., after which the mixture was slowly cooled to 40° C. and the precipitated riboflavin was filtered off under suction, washed neutral and dried.

The yield was 30 g, corresponding to 96.7% of theory, based on the crude product, and the purity was 100.1% (European Pharmacopeia).

We claim:

1. A process for the purification of crude riboflavin, comprising
    (a) dissolving said crude riboflavin in an aqueous solution of alkali metal hydroxide,
    (b) purifying said solution of riboflavin,
    (c) introducing said solution into a mixture of water and acid which is at about 90°–100° C., producing an acidic reaction mixture with a pH of about 6.5–0.8, while maintaining the resulting acidic reaction mixture at a temperature of about 90°–100° C.,
    (d) heating said acidic reaction mixture at about 90°–100° C. for a further 10–80 minutes, and
    (e) cooling said heated reaction mixture and isolating the crystallized riboflavin.

2. The process of claim 1, wherein said dissolving step comprises
    (a) suspending said crude riboflavin in water, and
    (b) adding an aqueous solution of an alkali metal hydroxide.

3. The process of claim 1, wherein said dissolving step comprises dissolving said crude riboflavin in a aqueous solution of an alkali metal hydroxide which has a concentration of about 0.16–0.63 molar.

4. The process of claim 1, wherein said purification step comprises treating said solution of riboflavin with active carbon or a filtration aid followed by filtration.

5. The process of claim 1, wherein said purification step comprises extracting said solution of riboflavin with an inert solvent which is insoluble or only slightly soluble in water.

6. The process of claim 1, comprising conducting said heating step while stirring.

7. The process of claim 1, wherein said dissolving and purifying steps are conducted at about 30°–45° C.

8. The process of claim 1, comprising adding bulk materials during said cooling step, said bulk materials being selected from the group consisting of corn starch, corn cob flour, fine soybean flour, wheat bran, $SiO_2$, calcium silicates, kieselguhr, steatite, talc and bolus alba.

9. The process of claim 1, wherein said acid has a pKa less than or equal to 4.76.

* * * * *